(12) United States Patent
McBride et al.

(10) Patent No.: US 10,267,807 B2
(45) Date of Patent: Apr. 23, 2019

(54) DIAGNOSIS AND/OR PROGNOSIS OF RENAL DYSFUNCTION

(75) Inventors: William Thomas McBride, Lisburn (GB); Marilyn Armstrong, Belfast (GB)

(73) Assignees: BELFAST HEALTH AND SOCIAL CARE TRUST, Belfast (GB); THE QUEEN'S UNIVERSITY OF BELFAST, Belfast (GB)

(*) Notice: Subject to any disclaimer, the term of this patent is extended or adjusted under 35 U.S.C. 154(b) by 96 days.

(21) Appl. No.: 12/937,593

(22) PCT Filed: Apr. 21, 2009

(86) PCT No.: PCT/GB2009/050404
§ 371 (c)(1),
(2), (4) Date: Dec. 7, 2010

(87) PCT Pub. No.: WO2009/130505
PCT Pub. Date: Oct. 29, 2009

(65) Prior Publication Data
US 2011/0071121 A1    Mar. 24, 2011

(30) Foreign Application Priority Data
Apr. 21, 2008 (GB) .................. 0807214.2

(51) Int. Cl.
| A61K 38/00 | (2006.01) |
| G01N 33/493 | (2006.01) |
| G01N 33/68 | (2006.01) |
| A61B 5/20 | (2006.01) |

(52) U.S. Cl.
CPC ... *G01N 33/6863* (2013.01); *G01N 2333/545* (2013.01); *G01N 2333/7151* (2013.01); *G01N 2800/347* (2013.01)

(58) Field of Classification Search
CPC .......... A61B 2018/00511; A61B 5/201; A61B 5/7275; A61B 5/00; A61B 5/412; G01N 33/6863
See application file for complete search history.

(56) References Cited

U.S. PATENT DOCUMENTS

| 5,041,381 A * | 8/1991 | Abrams et al. .......... 530/388.23 |
| 7,138,230 B2 * | 11/2006 | Hu et al. .......................... 435/4 |
| 7,141,382 B1 | 11/2006 | Parikh et al. |
| 7,476,497 B2 | 1/2009 | Hu et al. |
| 2005/0272101 A1 * | 12/2005 | Devarajan et al. .......... 435/7.9 |
| 2008/0076113 A1 | 3/2008 | Slotman |
| 2011/0071121 A1 | 3/2011 | McBride et al. |
| 2015/0183025 A1 | 7/2015 | Aoki |

FOREIGN PATENT DOCUMENTS

| EP | 1962092 A2 | 8/2008 |
| JP | 2012-506537 | 3/2012 |
| RU | 2302633 C1 | 7/2007 |
| WO | WO-2009130505 A1 | 10/2009 |

OTHER PUBLICATIONS

Opal et al. 2000. Chest 117:1162-1172.*
Ling et al. 2008. Nephron Clin Pract. 108:c176-c181.*
Gormley et al. 1999. Anesthesia and Analgesia. S78.*
Margel et al. 2011. European Urology 59:113-119.*
Bennett et al. 2008. Clin J. Am. Soc. Nephrol 3:665:673.*
Simerville et al. 2005. Am. Fam. Phys 71:1153-62.*
Su et al. 2012. J Biomed and Biotech 2012:1.*
Pelikanova et al 2003. Diabotologia 46:470-4.*
Makela et al. 2004. Am J. Kidney Disease. 43:809-816.*
Parikh et al. 2005. J. Am. Soc. Nephrol. 16:3046-3052.*
Shekar. 2006. Circulation 113:e51-e52.*
Han et al. 2008. Kidney International 73:863-869.*
Henkel, Gretchen et al., "Do Proinflammatory Cytokines Play a Role in Renal Dysfunction after Bypass?", Anesthesiology, Nov. 2000, 1 page.
Gormley, SM, et al., "Plasma and urinary cytokine homeostasis and renal dysfunction during cardiac surgery", Anesthesiology 2000;93(5):1210-6; discussion 5A.
Chertow, GM, Lazarus JM, Christiansen CL et al. "Preoperative Renal Risk Stratification". Circulation. 1997;95:878-884.
Lassnigg, A., Schmid ER., Hiesmayr M et al. "Impact of minimal increases in serum creatinine on outcome in patients after cardiothoracic surgery: Do we have to revise current definitions of acute renal failure?" Crit Care Med. 2008; 3, 4:1129-1137.
Mackensen, GB., Swaminathan M., Ti LK et al. "Preliminary report on the interaction of apolipoprotein E polymorphism with aortic atherosclerosis and acute nephropathy after CABG." Ann Thorac Surg 2004;78:520-526.
Stafford-Smith, M., Podgoreanu M., Swaminathan M et al. "Association of genetic polymorphisms with risk of renal injury after coronary bypass graft surgery." Am J Kidney Dis. 2005;45:519-530.
Mishra, J. Dent C., Tarabishi R et al. "Neutrophil gelatinase-associated lipocalin (NGAL) as a biomarker for acute renal injury after cardiac surgery." Lancet. 2005;365:1231-1238.

(Continued)

*Primary Examiner* — Shulamith H Shafer
(74) *Attorney, Agent, or Firm* — Winstead PC (57) ABSTRACT

The present invention relates to a method for diagnosing and/or prognosing renal dysfunction. The method comprises the steps of: —(a) determining the level of an anti-inflammatory cytokine present in a urine sample from a subject prior to physical trauma, prior to a hypotensive event, prior to sepsis, and/or prior to septic shock syndrome; (b) determining the level of the anti-inflammatory cytokine present in a urine sample from the subject following physical trauma, following or during a hypotensive event, following or during sepsis, and/or following or during septic shock syndrome; (c) calculating the difference between the level of the anti-inflammatory cytokine determined in step a) from the level of the anti-inflammatory cytokine determined in step b), and (d) providing a diagnosis and/or prognosis on the basis of a comparison between the difference calculated in step c) and the difference calculated in step c) when steps a) and b) are practiced on a control group.

7 Claims, 8 Drawing Sheets

(56) References Cited

OTHER PUBLICATIONS

Parikh, CR., Mishra J., Thiessen-Philbrook H et al. "Urinary IL-18 is an early predictive biomarker of acute kidney injury after cardiac surgery." Kidney Int. 2006;70:199-203.
McBride, WT., Allen S., Gormley SM et al. "Methylprednisolone favourable alters plasma and urinary cytokine homeostasis and subclinical renal injury at cardiac surgery." Cytokine. 2004;27:81-89.
Baker, RC., Armstrong MA., Allen SJ., McBride WT. "Role of the kidney in perioperative inflammatory responses." British Journal of Anaesthesia 2002; 88:330-334.
Chatterjee, PK., Hawksworth GM., McLay JS. "Cytokine-Stimulated Nitric Oxide Production in the Human Renal Proximal Tubule and Its Modulation by Natriuretic Peptides: A Novel Immunomodulatory Mechanism?" Exp Nephrol. 1999;7:438-448.
Hoste, EA., Kellum JA., Katz NM., Rosner MH., Haase M., Ronco C., "Epidemiology of Acute Kidney Injury." Contrib Nephrol. 2010;165:1-8.
Levey, AS., Bosch JP., Lewis JB., Greene T., Rogers N., Roth D. "A More Accurate Method to Estimate Glomerular Filtration Rate from Serum Creatinine: A New Prediction Equation." Modification of Diet in Renal Disease Study Group. Ann Intern Med. 1999;130:461-470.
Bouman, Catherine SC., Forni, LG., Joannidlis, M."Biomarkers and acute kidney injury: dining with the Fisher King?" Intensive Care Med (2010) 36:381-384 DOI 10.1007/s00134-009-1733-8.
Bagshaw, SM., Bennett, M., Haase, M., Haase-Fielitz, A., Egi, M., Morimatsu, H., D'amico, G., Goldsmith, D., Devarajan, P., Bellomo, R., "Plasma and urine neutrophil gelatinase-associated lipocalin in septic versus non-septic acute kidney injury in critical illness." Intensive Care Med (2010) 36:452-461 DOI 10.1007/s00134-009-1724-9.
Bhattacharyya, T., Iorio, R., and Healy, WL. "Rate of and Risk Factors for Acute Inpatient Mortality After Orthopaedic Surgery." J Bone Joint Surg Am. 2002;84:562-572.
Cruz, DN., de Cal, M., Garzotto, F., Perazella, MA., Lentini, P., Corradi, V., Piccinni, P., Ronco, C., "Plasma neutrophil gelatinase-associated, lipocalin is an early biomarker for acute, kidney injury in an adult ICU population.". Intensive Care Med (2010) 36:444-451 DOI 10.1007/s00134-009-1711-1.
Markewitz, BA., Michael JR., Kohan, DE. "Cytokine-induced Expression of a Nitric Oxide Synthase in Rat Renal Tubule Cells." J. Clin Invest. May 1993; 91, 2138-2143.
Chatterjee, PK., Hawksworth, GM., McLay, JS. "Cytokine-Stimulated Nitric Oxide Production in the Human Renal Proximal Tubule and Its Modulation by Natriuretic Peptides: A Novel Immunomodulatory Mechanism?" Exp Nephrol. Sep.-Dec. 1999;7(5-6):438-48.
Gormley SMC., McBride, WT., Armstrong, MA., McClean, E., MacGowan, SW., Campalani, G. McMurray, TJ., "Plasma and urinary cytokine homeostasis and renal function during cardiac surgery without cardiopulmonary bypass." Cytokine. Jan. 21, 2002;17(2):61-5.
Deng, J., Kohda, Y., Chiao, H., Wang, Y., Hu, X., Hewitt, SM., Miyaji, T., McLeroy, P., Nibhanupudy, B., Li, S., Star, RA. "Interleukin-10 inhibits ischemic and cisplatin-induced acute renal injury." Kidney Int. 2001, vol. 60, pp. 2118-2128.
Girndt, M., Kaul, H., Sester, U., Ulrich, C., Sester, M., Georg, T. and Kohler, H. "Anti-inflammatory interleukin-10 genotype protects dialysis patients from cardiovascular events." Kidney Int. 2002; 62(3):949-55.
Stenvinkel, P., Ketteler, M., Johnson, RJ., Lindholm, B., Pecoits-Filho, R., Riella, M., Heimburger, O., Cederholm, T., Girndt, M. "IL-10, IL-6, and TNF-a: Central factors in the altered cytokine network of uremia—The good, the bad, and the ugly." Kidney Int. Apr. 2005;67(4): 1216-1233.
Mu, W., Ouyang, X., Agarwal, A., Zhang, L., Long, DA., Cruz, PE., Roncal, CA., Glushakova, OY., Chiodo, VA., Atkinson, MA., Hauswirth, WW., Flotte, TR., Rodriguez-Iturbe, B., Johnson, RJ. "IL-10 Suppresses Chemokines, Inflammation, and Fibrosis in a Model of Chronic Renal Disease." J Am Soc Nephrol. Dec. 2005;16(12):3651-60. Epub Oct. 26, 2005.
McBride, WT., McBride SJ. "The balance of pro- and anti-inflammatory cytokines in cardiac surgery." Curr Opin Anaesthesiol. Feb. 1998;11(1): 15-22.
Impact of Renal Function Tests on Critical Care—Refining Point of Care Testing, Refining Point of Care Testing Strategies for Critical and Emergency Care. Quebec City, Quebec, Canada, Sep. 28-30, 2006.
Chirumamilla, Amala P. et al., "Outcome of Renal Insufficiency Patients Undergoing Coronary Artery Bypass Graft Surgery." Cardiology. 2008;111:23-29.
Stoyanov, Borislav., "International Search Report" for PCT/GB2009/050404 dated Jul. 17, 2009, 3 pages.
Litalien, Catherine et al., "Circulating inflammatory cytokine levels in hemolytic uremic syndrome", Pediatr Nephrol, 1999, 13:840-845.
Kopple, Joel D., "Nutritional status of patients with different levels of chronic renal insufficiency", Kidney International, vol. 36, Suppl. 27, 1989, pp. S-184-S-194.
Hirschberg, Raimund et al., "Effects of growth hormone and IGF-I on renal function", Kidney International, vol. 36, Suppl. 27, 1989, pp. S-20-S26.
Endre, Zoltan H. et al., "Early detection of acute kidney injury: Emerging new biomarkers", Nephrology 2008, 13, pp. 91-98.
Parikh, C.R. et al., "Urine NGAL and IL-18 are Predictive Biomarkers for Delayed Graft Function Following Kidney Transplantation", American Journal of Transplantation 2006, 6: 1639-1645.
Allen, Stephen J. et al., "Cell Salvage Alters the Systemic Inflammatory Response After Off-Pump Coronary Artery Bypass Grafting Surgery", 2007 by The Society of Thoracic Surgeons, Published by Elsevier Inc., Ann Thorac Surg 2007; 83: 578-85.
Allen, Stephen et al., "A clinical, renal and immunological assessment of Surface Modifying Additive Treated (SMART™) cardiopulmonary bypass circuits", Perfusion 2005: 20: 255-262.
Russell, J.C. et al., "The association between elevations in urinary cytokines and renal dysfunction after trauma and major surgery", British Journal of Anaesthesia 2003, 91: p. 463P.
Gormley, Sheena et al., "The effect of methylprednisolone on cytokine concentration and leukocyte adhesion molecule expression in an isolated cardiopulmonary bypass system", Cytokine 22, 2003, 149-155.
McBride, William T. et al., "Advances in cardiopulmonary bypass circuitry", Curr Opin Anaesthesiol 2003, 16: 27-31.
Brinkman, R. et al., "Acute Kidney Injury in Patients Undergoing Open Abdominal Aortic Aneurysm Repair: A Pilot Observation Trial", Journal of Cardiothoracic and Vascular Anesthesia, vol. 29 No. 5, Oct. 2015, pp. 1212-1219, electronic publication date Apr. 1, 2015.
Bihorac, A. et al., "Acute kidney injury is associated with early cytokine changes after trauma", J Trauma Acute Care Surg., vol. 74 No. 4, Apr. 2013, pp. 1005-1013.

\* cited by examiner

DIAGNOSIS AND/OR PROGNOSIS OF RENAL DYSFUNCTION

The present invention relates to a method for diagnosing and/or prognosing renal dysfunction.

Apart from the direct adverse impact of physical trauma on the body (e.g. from lesions caused by surgery or car crashes, or from surgical procedures such as blood bypass through a heart-lung machine), subjects suffering physical trauma often develop acute renal dysfunction. Other causes of a similar acute renal dysfunction include prolonged hypotensive states (associated with mucosal gut ischaemia and endotoxin translocation from gut to circulation), sepsis and septic shock syndromes.

In a population of patients who have normal renal function, diagnosis of post-trauma, hypotensive-induced, sepsis-induced, and/or septic shock syndrome-induced renal dysfunction can be made on the basis of a fall in Glomerular Filtration Rate (GFR) as compared with the normal or baseline GFR; as measured, for example by the MDRD test (explained in more detail below). The limitation of a diagnosis or prognosis based on such measurements is that it usually takes several days for MDRD estimated GFR values to fall. When the GFR fall is detected, it is often too late to institute therapeutic measures to obviate further deterioration in renal function. The challenge facing for example the peri-operative physician or intensive care physician is to identify a biological marker of renal dysfunction 48 hours before such dysfunction materialises (i.e. while there is still a possibility of preventative measures being taken in the intensive care unit; such as running such patients on supra-normal blood pressures, an intervention which in its own right is not without risk in the post-operative context, unless justified by the presence of an even greater risk of impending renal failure such as could be identified by the test according to the present invention).

It is well documented that trauma to the body induces an acute (often transient) plasma pro-inflammatory response. It has been shown that the magnitude of this acute plasma pro-inflammatory response correlates with post-trauma renal dysfunction (Gormley et al., Anesthesiology, 2000, 93). Other causes of a similar acute reno-toxic pro-inflammatory response include prolonged hypotensive states (associated with mucosal gut ischaemia and endotoxin translocation from gut to circulation), or sepsis and septic shock syndromes, all of which are usually either preceded by or associated with a systemic inflammatory response (SIRS) characterised by acute increases in pro-inflammatory mediators in the blood. A mechanism for how such acute pro-inflammatory responses when filtered from the blood damage renal tubules was suggested by Chatterjee who demonstrated in vitro that TNF-α applied to proximal tubules in cell culture leads to cell damage (Markewitz, J Clin Invest 1993; 91; Chatterjee et al., Exp Nephrol 1999; 7:438-8). Following challenge with the combination of inflammatory cytokines IL-1 beta, TNF-alpha, and IFN-gamma, in vitro proximal tubular cells exhibit a time-dependent increase in inducible NO synthase induction and corresponding NO production to cytotoxic concentration, an effect which was inhibited by L-NMMA (Chatterjee et al., Exp Nephrol 1999; 7:438-8). Stimulation of rat kidney epithelial cells with TNF-alpha and IFN-gamma dramatically increased the level of inducible nitric oxide synthase mRNA (Markewitz, J Clin Invest 1993; 91).

Numerous publications show that levels of urinary anti-inflammatory cytokines show dramatic increases after trauma, and in fact mirror the aforementioned increase in level of pro-inflammatory responses. See, for example: —Gormley et al. Cytokine, January 2002, 21 17(2). Further to this, it has been demonstrated that the magnitude of the post-trauma increases in anti-inflammatory cytokines correlate with the magnitude of renal injury and dysfunction. See, for example: —Litalien et al., Pediatr. Nephrol., November 1999, 13(9); Gretchen et al., Anesthesiology, November 2000, Gormley et al., Anesthesiology, 2000, 93; and; European Patent Publication No. 1 962 092 A (Renovar, Inc.). It is clear from the presentation of these results in the aforementioned publications that the dramatic increase in anti-inflammatory cytokines is proposed as a directly proportional marker for renal dysfunction.

The inventors were therefore surprised to find that when they analysed the urinary anti-inflammatory cytokine responses of a larger than previously analysed group of post-trauma subjects that a population of those subjects presented with only a modest or negligible anti-inflammatory cytokine response following physical trauma, as opposed to the expected dramatic rise in anti-inflammatory cytokine responses previously reported and as experienced by the majority of subjects. On further analysis of this sub-group, it was surprising to find that its members were at elevated risk of developing renal dysfunction when compared to those that showed the expected dramatic rise in urinary anti-inflammatory cytokine responses following physical trauma. Such findings are contrary to the previously accepted conclusion that post-trauma increases in urinary anti-inflammatory cytokines correlate with the magnitude of renal injury and dysfunction.

Not wishing to be restricted by theory, but in the interests of clarity, the inventors believe that the reason why the earlier studies suggested that urinary anti-inflammatory cytokines directly reflected renal injury was that the markers of renal injury that were used in those earlier studies were generally sub-clinical markers. It is now proposed by the present inventors that these sub-clinical markers did not necessarily reflect clinically significant renal dysfunction, because the nephrotoxic effects of the injurious stimulus which caused the sub-clinical injury were, in those patients that did well, adequately counteracted by a simultaneously generated adequate compensatory urinary anti-inflammatory immune response. Those patients who do not develop a compensatory adequate urinary anti-inflammatory immune response are the ones, it is proposed by the present inventors, that will go on to develop clinically significant renal injury; a hypothesis that cannot be developed from the previously available studies. In addition, because of financial constraints, the previous studies were practiced on a relatively small number of people (less than 30 persons) which meant that the sub-group of individuals with a poor compensatory anti-inflammatory response did not provide a statistically significant impact on the previously obtained results (the present study was practiced on almost 400 persons).

The inventors have, following extensive experimentation, provided evidence in support of the concept that by monitoring for a reduced level of anti-inflammatory cytokine response in a post-trauma or hypotensive subject, or in a subject suffering from sepsis or septic shock syndrome, one can arrive at a diagnostic and/or prognostic method for renal dysfunction.

Accordingly, in a first aspect of the present invention, there is provided a method for the diagnosis and/or prognosis of renal dysfunction induced by physical trauma, hypotension, sepsis and/or septic shock syndrome, wherein the method comprises the steps of:— a) determining the level of an anti-inflammatory cytokine present in a urine sample from a subject prior to physical trauma, prior to a hypotensive event, prior to sepsis, and/or prior to septic shock syndrome;

b) determining the level of the anti-inflammatory cytokine present in a urine sample from the subject following physical trauma, following or during a hypotensive event, following or during sepsis, and/or following or during septic shock syndrome;

c) calculating the difference between the level of the anti-inflammatory cytokine determined in step a) from the level of the anti-inflammatory cytokine determined in step b);

d) providing a diagnosis and/or prognosis on the basis of a comparison between the difference calculated in step c) and the difference calculated in step c) when steps a) and b) are practiced on a control group.

The control group is a group of individuals that do not have renal dysfunction on the fifth day following physical trauma, following or during a hypotensive event, following or during sepsis, and/or following or during septic shock syndrome (i.e. the control group represent the "normal" individual that does not develop renal dysfunction following trauma, a hypotensive event, sepsis, and/or septic shock syndrome). All of the control patients will have sustained some degree of sub-clinical renal injury but will have not had clinically significant renal injury. Determining whether or not an individual has renal dysfunction is a clinical question well within the abilities of the skilled person. However, in the interests of clarity, renal dysfunction is characterised by a reduction in the capacity to excrete metabolic products which accumulate systemically and are detectable clinicopathologically by renal function tests (in progressed states, renal dysfunction may be acute kidney failure, uremia or chronic renal damage). For example, the MDRD method of determining renal function is described below. The control group may experience the same or similar event (i.e. the same or similar trauma, hypotensive event, sepsis, and/or septic shock syndrome) to the subject being diagnosed.

The difference calculated in step c) when steps a) and b) are practiced on a control group may be a pre-determined value. The pre-determined value may be established from the following steps:— a') determining the level of the anti-inflammatory cytokine present in a urine sample from a control group prior to physical trauma, prior to a hypotensive event, prior to sepsis, and/or prior to septic shock syndrome;

b') determining the level of the anti-inflammatory cytokine present in a urine sample from the control group following physical trauma, following or during a hypotensive event, following or during sepsis, and/or following or during septic shock syndrome;

c') calculating the difference between the level of anti-inflammatory cytokine determined in step a') from the level of anti-inflammatory cytokine determined in step b').

In more detail, steps a'), b') and c') may comprise: —a') determining the average level of the anti-inflammatory cytokine present in a urine sample from individuals in a control group prior to physical trauma, prior to a hypotensive event, prior to sepsis, and/or prior to septic shock syndrome; b') determining the average level of the anti-inflammatory cytokine present in a urine sample from individuals in the control group following physical trauma, following or during a hypotensive event, following or during sepsis, and/or following or during septic shock syndrome, and; c') calculating the difference between the average level of anti-inflammatory cytokine determined in step a') from the average level of anti-inflammatory cytokine determined in step b'). The control group may comprise 30 individuals or more. The control group may comprise 300 individuals or more.

Based on the findings by the inventors, those subjects that present with a difference calculated in step c) that is smaller than the difference calculated in step c) when steps a) and b) are practiced on a control group are at greater than normal risk of developing renal dysfunction (i.e. such subjects are at an increased risk of developing renal dysfunction than those in the control group (i.e. normal individuals)). Such subjects may be at greater than normal risk of having renal dysfunction 5-days following physical trauma, following or during a hypotensive event, following or during sepsis, and/or following or during septic shock syndrome. Those subjects that present with a difference calculated in step c) that is the same or larger than the difference calculated in step c) when steps a) and b) are practiced on a control group are at a lesser than normal risk of developing renal dysfunction. Such subjects may be at lesser than normal risk of having renal dysfunction 5-days following physical trauma, following or during a hypotensive event, following or during sepsis, and/or following or during septic shock syndrome.

Subjects that present with a calculated difference at step c) that is progressively less than 100% that of the difference in step c) when steps a) and b) are practiced on a control group are at progressively greater than normal risk of developing renal dysfunction. Thus, when the difference calculated in step c) is 95% or less, 90% or less, 80% or less, 70% or less, 60% or less, 50% or less, 40% or less, 30% or less, 20% or less, or 10% or less that of the difference in step c) when steps a) and b) are practiced on a control group are at greater than normal risk of developing renal dysfunction. Such subjects may be at greater than normal risk of having renal dysfunction 5-days following physical trauma, following or during a hypotensive event, following or during sepsis, and/or following or during septic shock syndrome.

Not wishing to be restricted further, but in the interests of clarity, in one embodiment of the present invention when the difference calculated in step c) when steps a) and b) are practiced on a control group is 36000, 35500, 35000, 7500, 7600, 7800, 8000, or more pg of anti-inflammatory cytokine in one ml of urine greater than the difference calculated in c) (when step a) and b) are performed on the subject) then that subject is at greater than normal risk of developing renal dysfunction. Such subjects may be at greater than normal risk of having renal dysfunction 5-days following physical trauma, following or during a hypotensive event, following or during sepsis, and/or following or during septic shock syndrome.

Renal dysfunction induced by physical trauma, hypotension, sepsis and/or septic shock syndrome may be further characterised by pro-inflammatory responses that are induced following these events. Such inflammatory responses commonly follow the pattern of a classical systemic inflammatory response (SIRS). Thus, the renal dysfunction to be diagnosed/prognosed according to the present invention may be those that are induced by an acute (possibly transient) urinary pro-inflammatory response (for example, elevated urinary levels of IL-18 and/or of neturophil gelatinase-associated lipocalin (NGAL)).

The renal dysfunction to be diagnosed/prognosed may be early renal dysfunction, late renal dysfunction, or general renal dysfunction.

Such acute forms of renal dysfunction can be distinguished from autoimmune mediated chronic renal dysfunction, a condition that is clinically apparent over a prolonged period of time in parallel with the co-existing autoimmune condition (i.e. there is no requirement for a biological marker to predict the development of renal dysfunction occurring a few days later because the renal dysfunction is already well established).

A physical trauma is the impact on the body from external forces applied to the body, for example: —lesions caused by surgery or by blows or cuts to the body (such as might be experienced during a car crash), or; the impact on the blood as it interacts with the foreign surface of a heart-lung bypass machine. Renal dysfunction induced by physical trauma may be post-operative renal dysfunction. The post-operative renal dysfunction may be following cardiac, cardiovascular or cardiopulmonary surgery.

Whether or not an individual has hypotension is a clinical question and therefore well within the skill of an ordinary person in the art. For the avoidance of doubt however hypotension in adults may be defined as a systolic blood pressure <80 mmHg, or a mean arterial pressure (MAP)<50 mmHg. The hypotension may be prolonged, for example for over 2 hours.

Whether or not an individual has sepsis is a clinical question and therefore well within the skill of an ordinary person in the art. For the avoidance of doubt however, sepsis may be considered present if infection is highly suspected or proven and two or more of the following systemic inflammatory response syndrome (SIRS) criteria are met:
 1. Heart rate >90 beats per minute (tachycardia);
 2. Body temperature <36° C. (97° F.) or >38° C. (100° F.) (hypothermia or fever);
 3. Respiratory rate >20 breaths per minute or, on blood gas, a $P_aCO_2$ less than 32 mm Hg (4.3 kPa) (tachypnea or hypocapnia due to hyperventilation); and
 4. White blood cell count <4,000 cells/mm$^3$ or >12,000 cells/mm$^3$ (<4×10$^9$ or >12×10$^9$ cells/L), or greater than 10% band forms.

Whether or not an individual has septic shock is a clinical question and therefore well within the abilities of an ordinary person skilled in the art. For the avoidance of doubt however, septic shock may be defined by the presence of the following two criteria:
 1. Evidence of infection, through a positive blood culture; and
 2. Refractory hypotension—hypotension despite adequate fluid resuscitation and cardiac output. In adults it is defined as a systolic blood pressure <90 mmHg, or a MAP <60 mmHg, before institution of required resuscitative inotropic support, or a reduction of 40 mmHg in the systolic blood pressure from baseline. In children it is BP <2 SD of the normal blood pressure.

Whether or not an individual has SIRS is a clinical question and therefore well within the abilities of an ordinary person skilled in the art. For the avoidance of doubt however SIRS may be diagnosed when two or more of the following are present:
 1. Heart rate >90 beats per minute
 2. Body temperature <36 or >38° C.
 3. Tachypnea (high respiratory rate)>20 breaths per minute or, on blood gas, a $P_aCO_2$<4.3 kPa (32 mm Hg)
 4. White blood cell count <4000 cells/mm$^3$ or >12000 cells/mm$^3$ (<4×10$^9$ or >12×10$^9$ cells/L), or the presence of greater than 10% immature neutrophils.

Steps a) and/or a') may be preceded by a step of obtaining a urine sample from the subject or control group recited in steps a) and/or a'), respectively. In cases where the physical trauma, hypotensive event, sepsis, and/or septic shock syndrome is planned or can be predicted, for example surgical trauma, this may be relatively straightforward. Where the physical trauma, hypotensive event, sepsis, and/or septic shock syndrome is unexpected, for example when induced by a car crash, the step of determining the level of an anti-inflammatory cytokine present in a urine sample from a subject prior to these events (i.e. step a)) is achieved by using a control level for the anti-inflammatory cytokine. A control level is the level established to be the average (i.e. normal) human level of the anti-inflammatory cytokine in urine before physical trauma, hypotensive event, sepsis, and/or septic shock syndrome. Not wishing to be restricted further, but in the interest of clarity normal control values may be as follows: IL-1ra 6 000-10 000 pgml$^{-1}$ and TNFsr2 2 500-2 700 pgml$^{-1}$.

Steps b) and/or b') may be preceded by a step of obtaining a urine sample from the subject or control group recited in steps b) and/or b'), respectively. The urine sample analysed in steps b) and/or b') may be obtained from the subject/control group following physical trauma, hypotensive event, sepsis, and/or septic shock syndrome by less than 48, 36, 12, 6, 4 or 2 hours. The urine sample analysed in steps b) and/or b') may be obtained from the subject/control group following the physical trauma, hypotensive event, sepsis, and/or septic shock syndrome by between 2 to 48 hours, 4 to 36 hours, 6 to 24 hours, or 8 to 16 hours.

The anti-inflammatory cytokine may be any cytokine capable of suppressing inflammatory responses in the body and that can be detected in the urine. The anti-inflammatory cytokine may be one locally released in renal tissue. The anti-inflammatory cytokine may be TNFsr1, TNFsr2 or IL-1ra.

In one embodiment of the present invention, when the cytokine is TNFsr2 the difference calculated in step c) when steps a) and b) are practiced on a control group is 7500, 7600, 7800, 8000, or more pg of TNFsr2 in one ml of urine greater than the difference calculated in c) (when step a) and b) are performed on the subject) then that subject is at greater than normal risk of developing renal dysfunction. Such subjects may be at greater than normal risk of having renal dysfunction 5-days following physical trauma, following or during a hypotensive event, following or during sepsis, and/or following or during septic shock syndrome.

In one embodiment of the present invention, when the cytokine is IL-1ra the difference calculated in step c) when steps a) and b) are practiced on a control group is 36000, 35500, 35000, or more pg of IL-1ra in one ml of urine greater than the difference calculated in c) (when step a) and b) are performed on the subject) then that subject is at greater than normal risk of developing renal dysfunction. Such subjects may be at greater than normal risk of having renal dysfunction 5-days following physical trauma, following or during a hypotensive event, following or during sepsis, and/or following or during septic shock syndrome.

It has been found that basing the diagnosis and/or prognosis on the analysis of the levels of more than one type of anti-inflammatory cytokine can increase the sensitivity of the diagnostic or prognostic methods according to the present invention. For example, the methods according to the present invention may further comprise the steps of:—
 a") determining the level of one or more additional anti-inflammatory cytokine present in a urine sample from a subject prior to physical trauma, prior to a hypotensive event, prior to sepsis, and/or prior to septic shock syndrome;

b") determining the level of one or more additional anti-inflammatory cytokine present in a urine sample from the subject following physical trauma, following or during a hypotensive event, following or during sepsis, and/or following or during septic shock syndrome;

c") calculating the difference between the level of the one or more additional anti-inflammatory cytokine determined in step a") from the level of the one or more additional anti-inflammatory cytokine determined in step b"), and;

d") providing a diagnosis and/or prognosis on the basis of a comparison between the difference calculated in step c") and the difference calculated in step c") when steps a") and b") are practiced on a control group.

The diagnosis and prognosis being more sensitive when the comparison found in step d) and step d") are considered together. The risk of the subject developing renal dysfunction is greater when both (i) the difference calculated in step c) is smaller than the difference calculated in step c) when steps a) and b) are practiced on a control group, and (ii) the difference calculated in step c") is smaller than the difference calculated in step c") when steps a") and b") are practiced on a control group.

Any combination of the aforementioned anti-inflammatory cytokines may be used in such a method. For example the anti-inflammatory cytokine determined in steps a) and b) may be IL-1ra and the one or more anti-inflammatory cytokine determined in steps a") and b") may be TNFsr2.

Pro-inflammatory markers of impending renal dysfunction have been identified; pro-inflammatory mediators NGAL and IL-18 (Mishra et al., Lancet, 2005; 365:1231-38). Elevations of these substances in the urine of children have been associated with heightened risk of developing renal dysfunction several days later. Based on the hypothesis presented by the present inventors, however, establishing that an individual has an elevated pro-inflammatory response alone may not be sufficient to establish the risk of developing renal dysfunction.

Basing the diagnosis and/or prognosis on the analysis of the levels of one (or more than one type of) anti-inflammatory cytokine and one or more pro-inflammatory mediator can increase the sensitivity of the diagnostic or prognostic methods according to the present invention, and the sensitivity of those already known that are based on pro-inflammatory mediators alone. For example, the methods according to the present invention may further comprise the steps of:— a''') determining the level of one or more pro-inflammatory mediator present in a urine sample from a subject prior to physical trauma, prior to a hypotensive event, prior to sepsis, and/or prior to septic shock syndrome;

b''') determining the level of one or more pro-inflammatory mediator present in a urine sample from the subject following physical trauma, following or during a hypotensive event, following or during sepsis, and/or following or during septic shock syndrome;

c''') calculating the difference between the level of the one or more pro-inflammatory mediator determined in step a''') from the level of the one or more additional anti-inflammatory cytokine determined in step b'''), and;

d''') providing a diagnosis and/or prognosis on the basis of a comparison between the difference calculated in step c''') and the difference calculated in step c''') when steps a''') and b''') are practiced on a control group.

The diagnosis and prognosis being more sensitive when the comparison found in step d) and step d''') are considered together (even more sensitive when d, d" and d''' are considered together). For example, the risk of the subject developing renal dysfunction is greater when (i) the difference calculated in step c) is smaller than the difference calculated in step c) when steps a) and b) are practiced on a control group, and (ii) the difference calculated in step c''') is the same or greater than the difference calculated in step c''') when steps a''') and b''') are practiced on a control group.

The pro-inflammatory mediators may be any mediator capable of inducing an inflammatory response in the body, that is implicated in the development of renal dysfunction and that can be detected in the urine. The pro-inflammatory mediators may be IL-18 and/or NGAL.

In a further aspect of the present invention, there is provided a kit for use in the methods of the preceding claims, wherein the kit comprises:—

(a) one or more reagents for the detection of the amount of one or more anti-inflammatory cytokine;

(b) instructions for using the one or more reagents for detecting the one or more anti-inflammatory cytokines.

The kit may further comprise one or more reagents for the detection of one or more pro-inflammatory mediator, and instructions for using the one or more reagents for detecting the one or more pro-inflammatory mediator.

The kit may further comprise instructions for using the detecting of the one or more anti-inflammatory cytokines in order to arrive at a diagnosis or prognosis for renal dysfunction. In one embodiment the instructions are in accordance with the steps for diagnosis or prognosis of renal dysfunction provided in the first aspect of the present invention.

The kit may further comprise instructions for using the detecting of the one or more pro-inflammatory mediator in order to arrive at a diagnosis or prognosis for renal dysfunction. In one embodiment the instructions are in accordance with the steps for diagnosis or prognosis of renal dysfunction provided in the first aspect of the present invention.

As the instructions and reagents are to be capable of being used in order to practice the methods described above in accordance with the first aspect of the present invention, all features of the first aspect of the present invention may be included in the second aspect of the present invention, where the context permits. Consequently, for example, the anti-inflammatory cytokines (or combinations thereof) and the pro-inflammatory mediators mentioned in the first aspect of the present invention may be those recited above in the second aspect of the present invention.

In a third aspect of the present invention there is provided a method of treating renal dysfunction induced by physical trauma, hypotension, sepsis and/or septic shock syndrome, wherein the method includes the steps of: (i) diagnosing or prognosing renal dysfunction according to any of the methods of the first aspect of the present invention; and (ii) when the subject is identified to be at increased risk of developing renal dysfunction, applying therapeutic measures to treat or obviate the impending renal dysfunction. The advantage of such a method over current therapeutic interventions is that therapy may be administered at a stage when full renal failure may be prevented. The therapeutic measures applied in step (ii) may be: maintaining a supra-normal blood pressure; ensuring adequate tissue oxygen delivery; administration of steroids; renal replacement therapy; dialysis; or any combination thereof. A further advantage of this invention would be to allow intensive care managers to identify early in the intensive care stay of the patient those individuals who are likely to spend longer in intensive care than would otherwise be anticipated providing earlier planning for staff deployment.

The present invention will now be described, by way of example, with reference to the accompanying figures, in which:—

EXPERIMENTAL METHODS

Four hundred low risk (405) consecutive patients undergoing elective cardiac surgery were studied. The patients were recruited within the Cardiac Surgical Unit of the Royal Victoria Hospital Belfast (n=310) and the remainder from Papworth Everard Hospital in Cambridge England. All patients in the study underwent heart surgery of low risk with normal renal function preoperatively, including:
—coronary-artery bypass graft; off-pump coronary-artery bypass graft; heart valve surgery; coronary-artery bypass graft and heart valve surgery; coarctation of aorta; pericardiectomy. Other exclusion criteria include known dialysis dependant renal failure or significant renal disease prior to entrance into the study and diabetes mellitus. (Patients on preoperative ACE inhibitor therapy were not excluded from this study). Throughout the hospital stay normal daily clinical measures of major organ function were recorded. Data recorded in the patient notes and on the Biochemistry Laboratory database subsequently utilised in analysis. In addition to normal routine blood and urinary samples, additional urine samples will be obtained as follows:

Sample 1 obtained after residual urine has been discarded at catheterisation after anaesthesia induction.

Samples 2-5 obtained 2, 24, 48 and 72 hours following cessation of cardiopulmonary bypass. All urine samples assayed for TNF-sr2 and IL-1ra (at time points 1 and 3 as above; i.e. baseline and 24 hours post operation).

Cytokines Analysis (ELISA)

Cytokines are measured by R&D systems Quantikine solid phase ELISA technique. This system consists of a conjugate, standard, assay diluent, calibrator diluent, wash buffer concentrate, colour reagent A, colour reagent B, and a stop solution. Reagents should be at the room temperature before beginning the assay. The microplate-consists of 96 wells. This microplate is coated with capture antibody. To each well assay diluent is added. Standards in duplicate and the samples are added to the plate and incubated for 2 h at room temperature. Any analyte present in the sample is bound by the capture antibody (immobilized antibody). After the incubation, the plate is aspirated and washed four times with the supplied wash buffer to washout any unbound materials. After washing, horseradish protease (HRP) labelled detection antibody (conjugate) is added to the plate and further incubated at room temperature. Once again, after the incubation the plate is aspirated and washed 4 times. Any unbound detection antibody is washed away. In the next step prepared substrate solution tetramethylbenzidine (TMB) is added to the wells and a blue colour develops in proportion to the amount of analyte present in the sample. After 20 minutes incubation the colour develops (blue) proportional to the cytokine concentration. For analysis colour development is stopped turning the colour in the wells to yellow. The absorbance of the colour at 450 nm is measured which is read in the microplate reader.

Measurement of Renal Dysfunction

In 1989 Kopple et al as part of the Modification of Diet in Renal Disease study group published their findings investigating the impact of nutritional status on chronic renal insufficiency in 95 patients. The effects on progression of renal disease of a control diet of only mild dietary protein restriction were compared with 3 study diets of varying degrees of protein restriction and reduced phosphorus intake. The authors found that malnutrition and lower energy intake characterised patients with the lower GFR levels. There were some gender differences with men demonstrating a correlation between GFR and arm muscle area and percentage standard body weight especially at the onset of the experimental diets. In women, GFR correlated with dietary energy intake [Kopple et al., Kidney Int Suppl 1989; 27]. A logical development of this study from the MDRD group was the idea that analysis of patients' age weight, gender and ethnicity together with serum creatinine would allow GFR to be estimated. This assumption recognised that serum creatinine concentration alone does not adequately reflect renal function but should be considered along with the factors identified as influencing renal function in Kopple's study.

To develop the prediction equation 1628 patients were enrolled in the baseline period, of which 1070 were randomly selected as the training sample whereas the remaining 558 patients constituted the validation sample. The authors then used stepwise regression to the training sample to develop the equation which was then tested and compared with the Cockcroft and Gault formula and creatinine clearance measurements in the validation sample.

It was found that several measured variables were associated with a lower GFR. These included higher serum creatinine, higher serum urea and lower serum albumin levels concentrations. Independent variables associated with lower GFR included older age group, female gender and non-black ethnicity ($P<0.001$ for all factors).

The multiple regression models explained 90.3% of the variance in the logarithm of GFR in the validation sample. Measured creatinine clearance overestimated GFR by 19%, and creatinine clearance predicted by the Cockcroft-Gault formula overestimated GFR by 16%. After adjustment for this overestimation, the percentage of variance of the logarithm of GFR predicted by measured creatinine clearance or the Cockcroft-Gault formula was 86.6% and 84.2%, respectively.

MDRD study group estimated GFR is calculated from the following formula:

$$X = 32788 \times \text{creatinine}^{-1.154} \times \text{age}^{-0.203} \times \text{constant}$$

where the constant is 1 for white males, 0.724 for females, and 1.21 for African Americans.

MDRD estimated GFR in the present study was calculated from the above formula.

According to the above formula MDRD GFR was calculated at preop day 0 and at post operative days 1, 2 and 5. For each separate post op day as well as all post op days together patients can be divided into normal and abnormal renal function groups where "normal" and "abnormal" were defined by those who sustained falls in MDRD GFR of less than or greater than 15% of baseline respectively.

In summary then for each cytokine baseline and post surgery cytokine values were compared between the normal and abnormal groups where normality and abnormality were defined according to the 4 definitions mentioned below.

Definition 1: 'Abnormality' is defined as having day 1 MDRD >15% drop from baseline. (Early renal dysfunction).

Definition 2. 'Abnormality' is defined as having day 2 MDRD >15% drop from baseline. (Early renal dysfunction).

Definition 3. 'Abnormality' is defined as having day 5 MDRD >15% drop from baseline. (Late renal dysfunction).

Definition 4. 'Abnormality' is defined as having at least one MDRD value >15% drop from baseline during days 1, 2, and 5. (General renal dysfunction).

Results

Twenty percent of patients ($79/397$) were registered in the early renal dysfunction group (days 1 and 2). Of this subgroup it was found that by the fifth postoperative day 56 (71%) had got better and only 23 (29%) still had renal dysfunction. This shows that over two thirds of patients who have renal dysfunction in the first 48 hours postoperatively are better at 5 days post operatively.

Ten percent of all patients ($40/397$) were registered as having late renal dysfunction on the fifth postoperative day. Of this subgroup, 23 (57.5%) developed renal problems in the immediate postoperative period. However 17 of these 40 patients (42.5%) only showed their renal problems several days postoperatively despite normal post op renal function. This shows that over one third of patients with late renal dysfunction develop this complication without immediate postoperative signs of renal problems.

Cytokine Results

Changes in the cytokines from baseline are compared between normal and abnormal renal function groups. Renal function is defined according to the criteria provided above.

Figure 4:
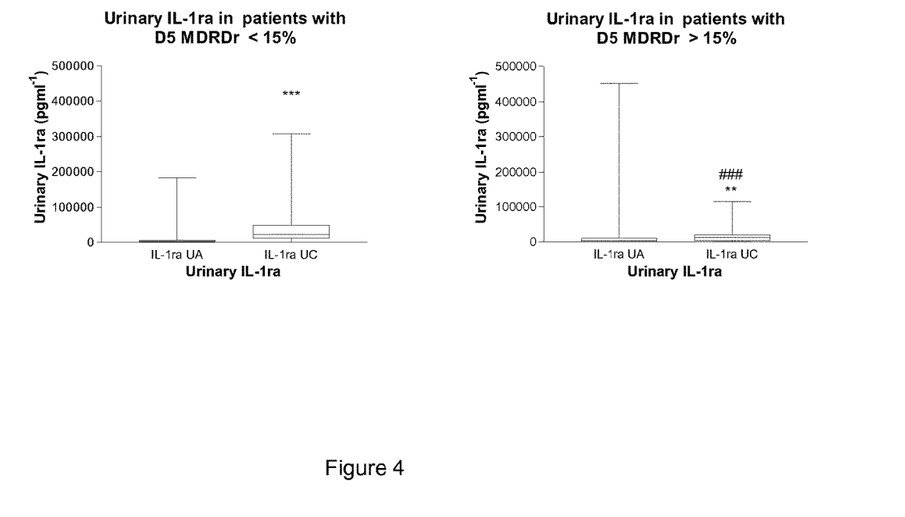
FIG. 4 shows a graph showing urinary IL-1ra at baseline (Sample UA) and 24 hours after revascularisation (Sample UC) in patients whose day 5 (D5) MDRD value was less than (n=347) or greater than (n=32) 15% drop from the preoperative baseline. Within group comparison was by Wilcoxon Signed rank (*P<0.001; P<0.01) and between group comparison at individual sampling times was by Mann Whitney test (###P<0.001).
Figure 5:
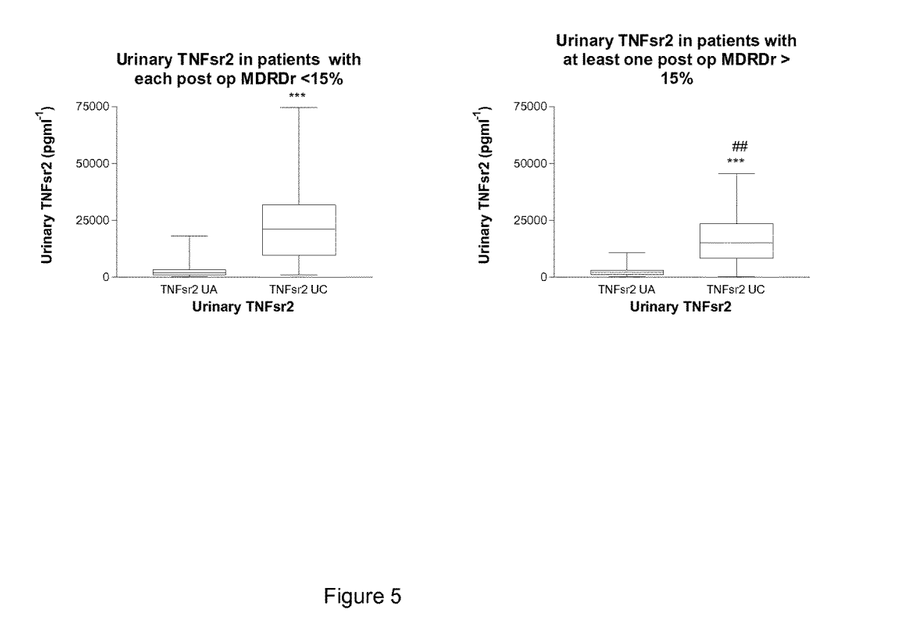
FIG. 5 shows a graph showing urinary TNFsr-2 at baseline (Sample UA) and 24 hours after revascularisation (Sample UC) in patients whose day 1, 2 and 5 MDRD values at any time were less than (n=301) or greater than (n=95) 15% drop from the preoperative baseline. Within group comparison was by Wilcoxon Signed rank (***P<0.001) and between group comparison at individual sampling times was by Mann Whitney test (##P<0.01).
Figure 8:
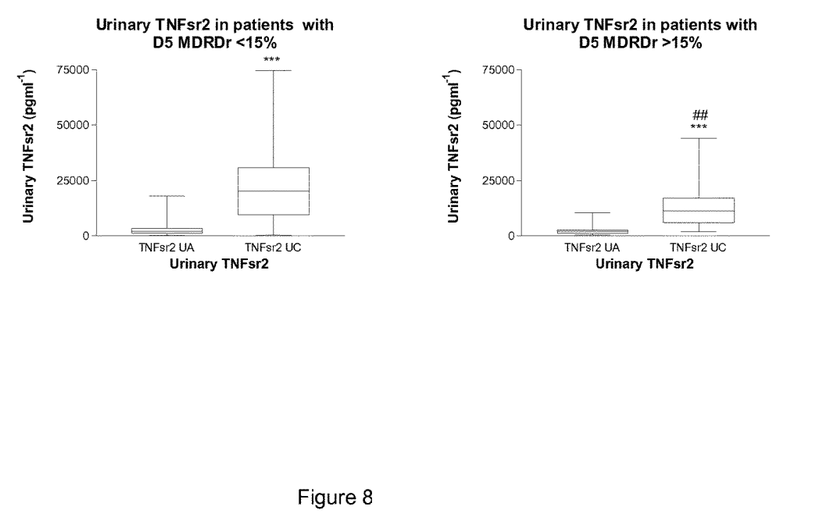
FIG. 8 shows a graph shows a graph showing urinary TNFsr-2 at baseline (Sample UA) and 24 hours after revascularisation (Sample UC) in patients whose day 5 (D5) MDRD value was less than (n=351) or greater than (n=37) a 15% drop from the preoperative baseline. Within group comparison was by Wilcoxon Signed rank (***P<0.001) and between group comparison at individual sampling times was by Mann Whitney test (##P<0.01).

(1) Urinary IL-1ra and Urinary TNFsr-2 24 Hours Post Operatively:

Patients who showed abnormal renal function on the fifth postoperative day (day 5 MDRD ratio >15%) (n=32) demonstrated as early as only 24 hours postoperatively a very significantly lower urinary anti-inflammatory response (urinary TNFsr-2 and IL-1ra at 24 hours post op) than those patients who later at day 5 showed normal renal function (n=347) (day 5 MDRD r<15%).

Figure 6:
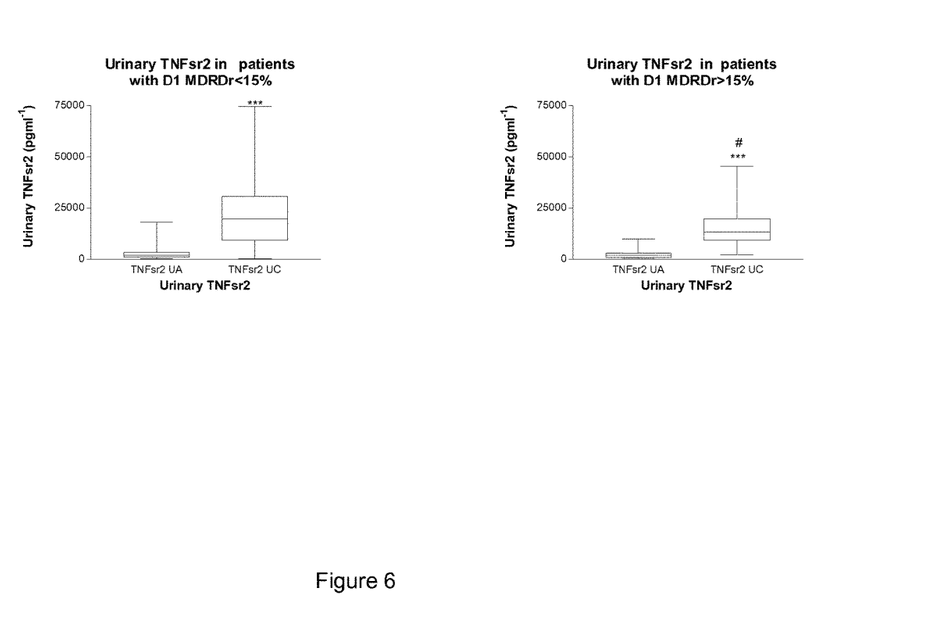
FIG. 6 shows a graph showing urinary TNFsr-2 at baseline (Sample UA) and 24 hours after revascularisation (Sample UC) in patients whose day 1 (D1) MDRD value was less than (n=360) or greater than (n=32) 15% drop from the preoperative baseline. Within group comparison was by Wilcoxon Signed rank (***P<0.001) and between group comparison at individual sampling times was by Mann Whitney test (#P<0.05).
Figure 7:
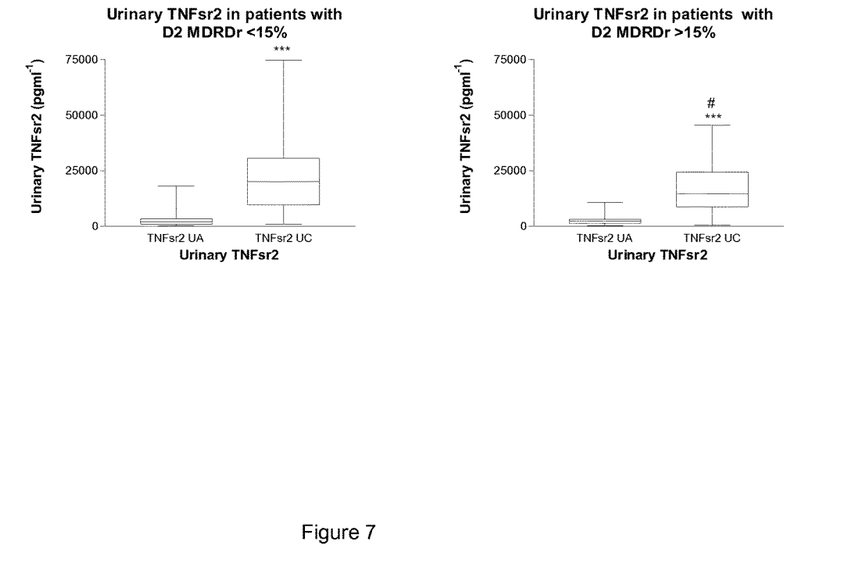
FIG. 7 shows a graph showing urinary TNFsr-2 at baseline (Sample UA) and 24 hours after revascularisation (Sample UC) in patients whose day 2 (D2) MDRD value was less than (n=323) or greater than (n=68) a 15% drop from the preoperative baseline. Within group comparison was by Wilcoxon Signed rank (***P<0.001) and between group comparison at individual sampling times was by Mann Whitney test (#P<0.05).

(2) Urinary IL-1ra and TNF-sr2:

Patients who showed abnormal renal function on the first and second postoperative days (day 1-2 MDRD ratio >15%) (n=32 on day 1; n=68 on day 2) demonstrated as early as only 24 hours postoperatively a significantly lower urinary anti-inflammatory TNF-sr2 than those patients who showed normal renal function on days 1 and 2 (day 1-2 MDRD r<15%) (n=360 day 1; n=323 day 2).

This shows that urinary TNF-sr2 is reduced in the urine of those patients who had early (days 1 and 2) as well as late (day 5) renal dysfunction.

Figure 1:
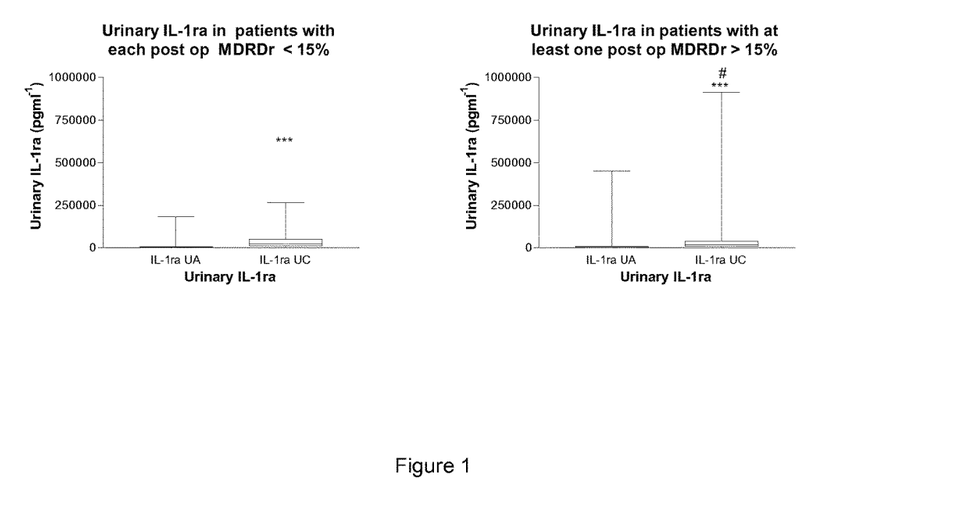
FIG. 1 shows a graph showing urinary IL-1ra at baseline (Sample UA) and 24 hours after revascularisation (Sample UC) in patients whose day 1, 2 and 5 MDRD values at any time were less than (n=297) or greater than (n=94) 15% drop from the preoperative baseline. Within group comparison was by Wilcoxon Signed rank (***P<0.001) and between group comparison at individual sampling times was by Mann Whitney test (#P<0.05).
Figure 2:
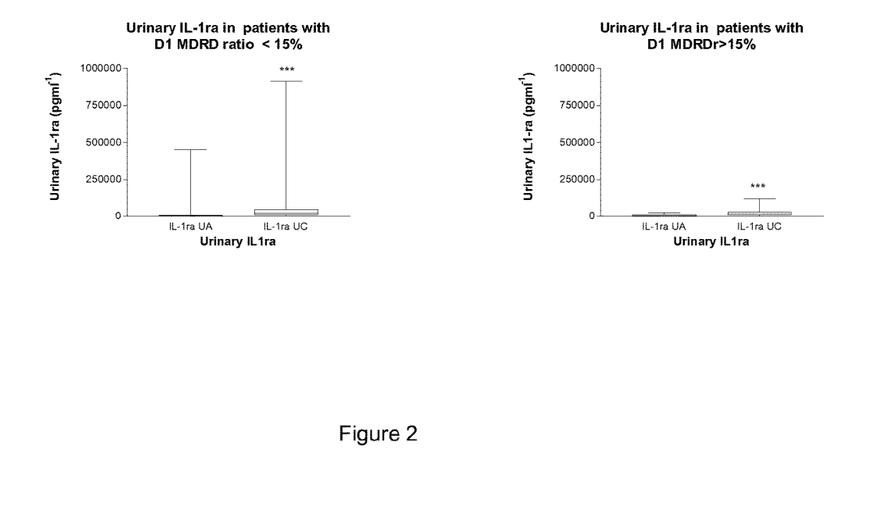
FIG. 2 shows a graph showing urinary IL-1ra at baseline (Sample UA) and 24 hours after revascularisation (Sample UC) in patients whose day 1 (D1) MDRD value was less than (n=351) or greater than (n=32) 15% drop from the preoperative baseline. Within group comparison was by Wilcoxon Signed rank (***P<0.001) and between group comparison at individual sampling times was by Mann Whitney test (P>0.05).
Figure 3:
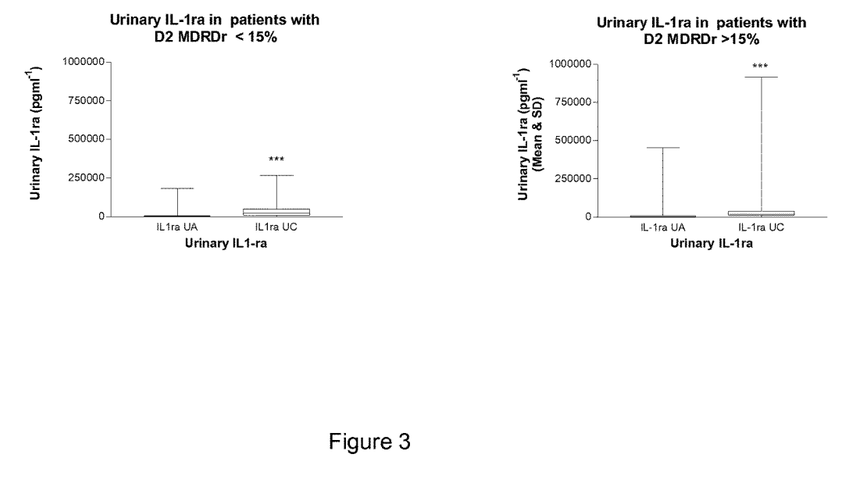
FIG. 3 shows a graph showing urinary IL-1ra at baseline (Sample UA) and 24 hours after revascularisation (Sample UC) in patients whose day 2 (D2) MDRD value was less than (n=314) or greater than (n=68) 15% drop from the preoperative baseline. Within group comparison was by Wilcoxon Signed rank (***P<0.001) and between group comparison at individual sampling times was by Mann Whitney test (P>0.05).

There was no significant difference in 24 hour urinary anti-inflammatory IL-1ra between those patients who at day 1 and 2 showed abnormal renal function as compared with those who had normal renal function in the same period.

Urinary TNF-sr2 at 24 hours was significantly lower in the renal dysfunction group of days 1 and 2 whereas urinary IL-1ra in the same time period was not significantly lower in the renal dysfunction group.

(3) The Cytokine Profile which Characterises Early Renal Dysfunction:

Our results show that early postoperative renal dysfunction at days 1 and 2 have a 24 hour post operative cytokine profile characterised by decreases in the 24 hour post op urinary TNF-sr2 response but not IL-1ra.

(4) The Cytokine Profile which Characterises Late Renal Dysfunction:

Renal dysfunction developing much later around day 5 post operatively has a different cytokine profile being characterised by very significant reductions in the 24 hour post operative urinary IL-1ra and TNF-sr2 responses.

The invention claimed is:

1. A method for the prognosis of renal dysfunction by detecting a difference in the level of an anti-inflammatory cytokine present in a urine sample from a subject prior to a planned physical trauma and following the planned physical trauma, said method comprising:

a) obtaining a urine sample from a human subject prior to the planned physical trauma;
b) detecting the anti-inflammatory cytokine present in the urine sample obtained in step a), wherein the anti-inflammatory cytokine is selected from the group consisting of IL-1ra, TNFsr1 and TNFsr2 and any combination thereof;
c) obtaining a urine sample from a human subject within 48 hours following the planned physical trauma;
d) detecting the anti-inflammatory cytokine present in the urine sample obtained in step c), wherein the anti-inflammatory cytokine is selected from the group consisting of IL-1ra, TNFsr1 and TNFsr2 and any combination thereof;
e) calculating the difference in the levels of the anti-inflammatory cytokine determined in step b) and step d), wherein those subjects that present with a difference calculated in step e) that is smaller than the difference calculated in step e) when steps b) and d) are practiced on a control group, are at greater risk of developing renal dysfunction relative to the control group, wherein the control group consists of individuals who do not have renal dysfunction on the fifth day following the planned physical trauma; and
f) applying therapeutic measures to treat or obviate impending renal dysfunction, wherein the therapeutic measures to treat or obviate impending renal dysfunction are selected from maintaining supra-normal blood pressure, ensuring adequate tissue oxygen delivery, administration of steroids, renal replacement therapy, dialysis or any combination thereof.

2. The method as claimed in claim 1, wherein the renal dysfunction is acute renal dysfunction.

3. The method as claimed in claim 1, wherein the urine sample analyzed in step c) is obtained from the subject between 2 hours and 48 hours following the planned physical trauma.

4. The method of claim 1 further comprising the steps of:
f) detecting the level of one or more additional anti-inflammatory cytokines present in a urine sample from the subject prior to the planned physical trauma;
g) detecting the level of one of more additional anti-inflammatory cytokines present in a urine sample from the subject following the planned physical trauma; and
h) calculating the difference between the level of the one or more additional anti-inflammatory cytokines determined in step f) from the level of the anti-inflammatory cytokines determined in step g) wherein those subjects that present with a difference calculated in step h) that is smaller than the difference calculated in step h) when steps f) and g) are practiced on a control group, are at greater risk of developing renal dysfunction relative to the control group, wherein the control group consists of individuals who do not have renal dysfunction on the fifth day following the planned physical trauma.

5. The method as claimed in claim 1, further comprising the steps of:
a''') detecting the level of one or more pro-inflammatory mediator present in a urine sample from a subject prior to the planned physical trauma, wherein the one or more pro-inflammatory mediator is IL-18 or neutrophil gelatinase-associated lipocalin (NGAL);
b''') detecting the level of one or more pro-inflammatory mediator present in a urine sample from the subject following the planned physical trauma;
c''') calculating the difference between the level of the one or more pro-inflammatory mediator determined in step a''') from the level of the one or more additional pro-inflammatory mediator determined in step b'''); and
d''') comparing the difference calculated in step c''') and the difference calculated in step c''') when steps a''') and b''') are practiced on a control group, wherein there is an increased risk of developing renal dysfunction when the difference between the pre- and post-event proinflammatory cytokine level for a test group is greater than that experienced by the control group.

6. The method as claimed in claim 1, wherein when the cytokine is IL-1ra, and the difference calculated in step e) when steps a) and b) are practiced on a control group is 35000 or more pg of IL-1ra in one ml of urine greater than the difference calculated in step e), the subject is at greater than normal risk of developing renal dysfunction.

7. A method for the prognosis of renal dysfunction by detecting a difference in the level of an anti-inflammatory cytokine present in a urine sample from a subject prior to surgery and following the syndrome surgery, said method comprising:
a) obtaining a urine sample from a human subject prior to the surgery;
b) detecting the anti-inflammatory cytokine present in the urine sample obtained in step a), wherein the anti-inflammatory cytokine is selected from the group consisting of IL-1ra, TNFsr1 and TNFsr2 and any combination thereof;
c) obtaining a urine sample from a human subject within 48 hours following the surgery;
d) detecting the anti-inflammatory cytokine present in the urine sample obtained in step c), wherein the anti-inflammatory cytokine is selected from the group consisting of IL-1ra, TNFsr1 and TNFsr2 and any combination thereof;
e) calculating the difference in the levels of the anti-inflammatory cytokine determined in step b) and step d), wherein those subjects that present with a difference calculated in step e) that is smaller than the difference calculated in step e) when steps b) and d) are practiced on a control group, are at greater risk of developing renal dysfunction relative to the control group, wherein the control group consists of individuals who do not have renal dysfunction on the fifth day following the surgery; and
f) applying therapeutic measures to treat or obviate impending renal dysfunction, wherein the therapeutic measures to treat or obviate impending renal dysfunction are selected from maintaining supra-normal blood pressure, ensuring adequate tissue oxygen delivery, administration of steroids, renal replacement therapy, dialysis or any combination thereof.

* * * * *